United States Patent
Fryshman

(10) Patent No.: US 10,026,165 B1
(45) Date of Patent: Jul. 17, 2018

(54) OBJECT IMAGE RECOGNITION AND INSTANT ACTIVE RESPONSE

(71) Applicant: Bernard Fryshman, Brooklyn, NY (US)

(72) Inventor: Bernard Fryshman, Brooklyn, NY (US)

( * ) Notice: Subject to any disclaimer, the term of this patent is extended or adjusted under 35 U.S.C. 154(b) by 0 days.

(21) Appl. No.: 15/919,541

(22) Filed: Mar. 13, 2018

Related U.S. Application Data

(63) Continuation-in-part of application No. 15/802,814, filed on Nov. 3, 2017, now Pat. No. 9,965,850, which
(Continued)

(51) Int. Cl.
*G06T 7/00* (2017.01)
*A01H 1/02* (2006.01)
(Continued)

(52) U.S. Cl.
CPC ........... *G06T 7/0008* (2013.01); *A01H 1/025* (2013.01); *A01M 1/026* (2013.01); *A01M 1/06* (2013.01); *A01M 1/14* (2013.01); *A01M 1/20* (2013.01); *A01M 1/2094* (2013.01); *A01M 1/22* (2013.01); *A01M 1/226* (2013.01); *A01M 3/005* (2013.01); *A01M 3/007* (2013.01); *A01M 5/02* (2013.01); *A01M 5/04* (2013.01); *A01M 7/00* (2013.01); *A01M 99/00* (2013.01); *B64C 39/024* (2013.01); *B64D 1/18* (2013.01); *G06K 9/00* (2013.01); *G06K 9/6256* (2013.01); *G06K 9/6267* (2013.01); *G06T 7/0004* (2013.01); *H04N 5/2252* (2013.01); *H04N 5/2253* (2013.01); *H04N 7/185* (2013.01); *B64C 2201/027* (2013.01); *B64C 2201/12* (2013.01); *G06K 2209/17* (2013.01); *G06T 2207/10024* (2013.01); *G06T 2207/10032* (2013.01); *G06T 2207/10056* (2013.01); *G06T 2207/20081* (2013.01); *G06T 2207/30128* (2013.01); *Y10S 901/01* (2013.01); *Y10S 901/09* (2013.01); *Y10S 901/40* (2013.01); *Y10S 901/41* (2013.01)

(58) Field of Classification Search
CPC combination set(s) only.
See application file for complete search history.

(56) References Cited

U.S. PATENT DOCUMENTS

| | | | |
|---|---|---|---|
| 6,508,033 B2 * | 1/2003 | Hessel | A01B 79/005 47/60 |
| 6,671,582 B1 * | 12/2003 | Hanley | A01B 51/02 250/339.11 |

(Continued)

*Primary Examiner* — Anand Bhatnagar
(74) *Attorney, Agent, or Firm* — Bell & Manning, LLC

(57) ABSTRACT

A device for use in a security system includes a sensor, an image capture device, an action arm, and a processor in communication with the sensor, the image capture device, and the action arm. The processor is configured to receive data from the sensor and the image capture device and identify a target based on an analysis of the received data. The processor is also configured to determine, based on the analysis of the received data, that the target is a drone or other mechanical device. The processor is also configured to determine an action to take on the identified target. The processor is further configured to cause the action arm to perform the determined action on the target.

20 Claims, 6 Drawing Sheets

Related U.S. Application Data is a continuation-in-part of application No. 15/654,390, filed on Jul. 19, 2017, now Pat. No. 9,852,362, which is a continuation-in-part of application No. 15/425,079, filed on Feb. 6, 2017, now Pat. No. 9,811,764, which is a continuation of application No. 15/153,621, filed on May 12, 2016, now Pat. No. 9,563,945, which is a continuation-in-part of application No. 14/733,044, filed on Jun. 8, 2015, now Pat. No. 9,381,646, which is a continuation-in-part of application No. 14/505,430, filed on Oct. 2, 2014, now Pat. No. 9,053,528, which is a continuation-in-part of application No. 13/542,416, filed on Jul. 5, 2012, now Pat. No. 8,855,374.

(60) Provisional application No. 62/551,345, filed on Aug. 29, 2017, provisional application No. 62/183,591, filed on Jun. 23, 2015, provisional application No. 61/504,462, filed on Jul. 5, 2011.

(51) Int. Cl.

| | | |
|---|---|---|
| *B64D 1/18* | (2006.01) | |
| *B64C 39/02* | (2006.01) | |
| *H04N 7/18* | (2006.01) | |
| *A01M 7/00* | (2006.01) | |
| *G06K 9/62* | (2006.01) | |
| *H04N 5/225* | (2006.01) | |
| *G06K 9/00* | (2006.01) | |
| *A01M 3/00* | (2006.01) | |
| *A01M 1/22* | (2006.01) | |
| *A01M 1/20* | (2006.01) | |
| *A01M 1/14* | (2006.01) | |
| *A01M 1/06* | (2006.01) | |
| *A01M 1/02* | (2006.01) | |
| *A01M 5/04* | (2006.01) | |
| *A01M 5/02* | (2006.01) | |
| *A01M 99/00* | (2006.01) | |

(56) References Cited

U.S. PATENT DOCUMENTS

| | | | |
|---|---|---|---|
| 7,854,108 B2 * | 12/2010 | Koselka | A01D 46/30 56/10.2 A |
| 8,381,501 B2 * | 2/2013 | Koselka | A01D 46/30 56/10.2 A |
| 9,816,783 B1 * | 11/2017 | Means | F41G 3/26 |
| 2013/0192451 A1 * | 8/2013 | Scott | F41G 3/00 89/41.05 |
| 2017/0015418 A1 * | 1/2017 | Matus | B64C 39/024 |
| 2017/0255198 A1 * | 9/2017 | Rodriguez | G05D 1/0088 |
| 2017/0322655 A1 * | 11/2017 | Stafford | G06F 3/017 |
| 2018/0001476 A1 * | 1/2018 | Tan | B61G 7/04 |
| 2018/0027772 A1 * | 2/2018 | Gordon | A01K 15/023 |
| 2018/0046189 A1 * | 2/2018 | Kim | G05D 1/0094 |

\* cited by examiner

OBJECT IMAGE RECOGNITION AND INSTANT ACTIVE RESPONSE

CROSS-REFERENCE TO RELATED APPLICATIONS

The present application claims priority as a continuation-in-part application of U.S. patent application Ser. No. 15/802,814 filed on Nov. 3, 2017, which claims priority to U.S. Patent App. No. 62/551,345 filed on Aug. 29, 2017. U.S. patent application Ser. No. 15/802,814 is also a continuation-in-part of U.S. patent application Ser. No. 15/654,390 filed on Jul. 19, 2017 (now U.S. Pat. No. 9,852,362), which is a continuation-in-part of U.S. patent application Ser. No. 15/425,079 filed on Feb. 6, 2017 (now U.S. Pat. No. 9,811,764), which is a continuation of U.S. patent application Ser. No. 15/153,621 filed on May 12, 2016 (now U.S. Pat. No. 9,563,945), which claims priority to U.S. Patent App. No. 62/183,591 filed on Jun. 23, 2015. U.S. patent application Ser. No. 15/153,621 is also a continuation-in-part of U.S. patent application Ser. No. 14/733,044 filed on Jun. 8, 2015 (now U.S. Pat. No. 9,381,646), which is a continuation-in-part of U.S. patent application Ser. No. 14/505,430 filed on Oct. 2, 2014 (now U.S. Pat. No. 9,053,528), which is a continuation-in-part of U.S. patent application Ser. No. 13/542,416 filed on Jul. 5, 2012 (now U.S. Pat. No. 8,855,374), which claims priority to U.S. Patent App. No. 61/504,462 filed on Jul. 5, 2011. Each of these priority applications is incorporated herein by reference in their entirety.

BACKGROUND

The decreased use of pesticides on the one hand and the decreased effectiveness of those which are in use on the other, has resulted in a disturbing proliferation of insects in food and in the home. Moreover, insects and other invading offending objects frequently infest orchards or similar crops, which can cause crop damage and decreased yields. Other types of offending objects can include aircraft such as drones that are used for spying and planning military operations. Some drones have been designed to include firearms that are used to attack targets in military zones.

SUMMARY

In one embodiment, described herein is a computer image analysis system, which captures an image of a substrate or other area to be checked for offending objects and is trained to recognize various offending objects commonly associated with such substrates to be checked. If an offending object is identified any of various action operations are taken in different embodiments described herein, including removal of the offending object by way of an action head associated with an imaging device. Another action operation can include destroying the offending object by the action head. In some embodiments, the system is positioned on a movable platform to scan a wide area for offending objects and/or to perform mitigation actions once an offending object is detected.

An illustrative device for use in a security system includes a sensor, an image capture device, an action arm, and a processor in communication with the sensor, the image capture device, and the action arm. The processor is configured to receive data from the sensor and the image capture device and identify a target based on an analysis of the received data. The processor is also configured to determine, based on the analysis of the received data, that the target is a drone or other mechanical device. The processor is also configured to determine an action to take on the identified target. The processor is further configured to cause the action arm to perform the determined action on the target.

An illustrative method for implementing a security system includes receiving, by a sensor on a device, first data indicative of a target. The method also includes receiving, by an image capture device of the device, second data indicative of the target, wherein the second data comprises image data. The method also includes identifying, by a processor in communication with the sensor and the image capture device, a presence of the target based on an analysis of the received first data and second data. The method also includes determining, by the processor and based on the analysis of the received data, that the target is a drone or other mechanical device. The method also includes determining, by the processor, an action to take on the identified target. The method further includes performing, by an action arm of the device that is in communication with the processor, the determined action on the target.

Other principal features and advantages of the invention will become apparent to those skilled in the art upon review of the following drawings, the detailed description, and the appended claims.

BRIEF DESCRIPTION OF THE DRAWINGS

Illustrative embodiments will hereafter be described with reference to the accompanying drawings, wherein like numerals denote like elements. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Embodiments of the present subject matter will now be described with reference to the above-identified figures. However, the drawings and the description herein are not intended to limit the scope of the invention. It will be understood that various modifications of the present description are possible without departing from the spirit of the invention. Also, features or operations described herein may be omitted, additional operations or features may be included, and/or features or operations described herein may be combined in a manner different from the specific combinations recited herein without departing from the spirit of the invention.

In one illustrative embodiment, a lens is used to point at a leaf of lettuce and capture an enlarged image thereof via an image capturing device. The image may be stored in digital memory for later analysis or it may be analyzed in real time. In either case, the image is sent to a processor that is trained to recognize the general characteristics and color of the lettuce, and which is also trained to recognize physical characteristics and features of insects typically found on lettuce. The image is magnified so that the presence of the insect, even if well hidden, will be identified by comparison with a library of insects stored in memory. In one embodiment, the processor does not positively identify a bug or other identifiable foreign object, but it may recognize the object as foreign. For instance, a processor may contain parameters of acceptable color values or hues for a specific substrate and if an object is outside of such parameters—software running on the processor determines the object as "foreign."

The identification of the insect can immediately trigger a response in an action head which is attached to the lens housing and is capable of moving to the insect position, and removing or destroying the insect automatically. In another embodiment, rather than removing an observed insect—an action head grips the piece of lettuce and discards it.

Figure 1:
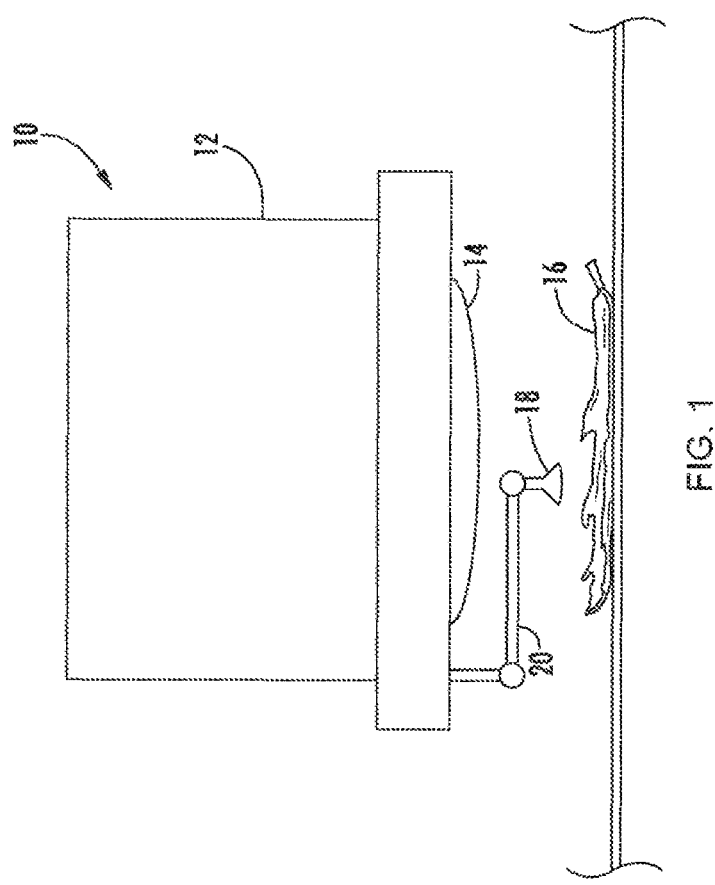
FIG. 1 shows a schematic side view of a scanning device disposed above a substrate to be checked according to an illustrative embodiment.

FIG. 1 shows a scanning device having a casing 12, which houses an image recognition system. A downward facing microscope, lens 14 or any such image capturing device and magnification device is located at a bottom portion of the scanning device. As shown, the lens 14 is directed at a substrate 16, such as, for example, a piece of lettuce. The lens magnifies a segment of a substrate to be checked and it feeds captured images to an image recognition system for image analysis. Images may be stored on a digital storage medium, among other storage systems or media.

It will be understood by those of ordinary skill in the art that the device 10 may be provided with a plurality of differently powered lenses which may be automatically adjusted when greater focusing ability is needed and any of different image capturing devices may be utilized, such as for example, a camera or a video camera, a video telescope, a video monocular, or an array thereof. It should also be understood that the image recognition system need not be housed within the casing 12 of the device—but rather the image recognition software may be provided at a location that is distant from the image-capturing device. In such embodiment, an image-capturing device (e.g. a microscope lens coupled to an image capturing system) is utilized to capture images. The images are then sent by a wired or wireless connection to an image classifier.

FIG. 1 shows an action head 18, which is provided at the distal end of a movable arm 20. The action head may be equipped with one or more instruments, such as a gripping device and/or a suctioning device. In another embodiment described herein, the action head is provided with a heating element or similar heat source—which can destroy a bug or a segment of lettuce when it is brought into direct contact therewith.

In one embodiment, the device 10 housing the lens 14 and action head 18 is a handheld unit, which may be manually or automatically moved across a stationary substrate such as a leaf of lettuce. In another embodiment the device 10 is mounted on a stationary support structure and a conveyor belt positioned below the device delivers items to be scanned below the microscope lens of the device. Still in other embodiments, the device is mounted to a linear motion track and it incrementally moves (for instance by incremental movements of a rack and pinion wheel controlled by a computer) across a substrate to be searched. In one embodiment, the device 10 may be used for purposes of "surveillance." In this embodiment, the device is mounted in a fixed position. When an offending object (such as an insect) enters the field of vision of the lens and is recognized as such by the image recognition system—a command is sent to activate the action head 18 to eliminate and/or neutralize the offending object. It is to be understood that as an alternative to eliminating and/or neutralizing an offending object, the device could mark the offending object for subsequent removal or remedial action. In some embodiments, device 10 may be a drone, which may be a remotely controlled and/or autonomously controlled vehicle (e.g., aircraft, ground vehicle). For example, an autonomous vehicle may be operated according to pre-programmed rules, such as navigation directions (e.g., coordinates or street directions), and/or logical rules to govern operation, such as obstacle avoidance rules and/or task execution rules (e.g., using a scanning or imaging device to assess various subjects).

It should be further understood that the moveable arm described herein may be its own detached unit, but which operates under the control of the software, which software may be stored in memory on the device 10 and configured to run on one or more processors, or which software may be remotely located, such as on a remote server accessible via a data communication signals and/or data networks. An illustrative device control system is described herein with reference to FIG. 4.

In an illustrative embodiment, action head 18 is mounted on an exterior surface of a device such as a drone, a vehicle, or the like. In other embodiments, action head 18 is attached to the distal end of a movable arm. It will be understood that a movable arm may be any of various structures such as, for example, one or more linear guide tracks, rack and pinion systems or such similar relative motion mechanism for supporting and moving an action head. The arm is movable in any of various directions by way of ball joints, linear motion tracks or other such similar movement systems. When a bug or other offending object is detected by the image recognition system, the software is programmed to send a signal to the moveable arm. The moveable arm is then controlled by a software application and directed to the located bug. The action head is deployed to either destroy the bug as described above or to suction it off of the substrate. In one embodiment, rather than directing the action head to a specific location—the moveable arm is directed to push the piece of lettuce (or other substrate) away, thereby discarding the same or removing it from a batch.

The computer used to control operations, execute routines and store data may include at least one or more processors and memory storage devices. The computer also may receive a number of inputs and outputs for communicating information externally.

It is to be understood that the computer which operates the device may operate under the control of an operating system and software applications, components and programs that execute the routines and systems described herein. In general, the routines executed to implement the embodiments, whether implemented as part of an operating system or a specific application, component, program, object, module or sequence of instructions will be referred to herein as "the system", or "software". The software controls the image acquisition, image storage, image analysis and movements of the arm, action head and/or the movement of the device along a track.

It is further to be understood by those of ordinary skill in the art that the described apparatus can include image capturing capabilities and image recognition capabilities coupled with software that is programmed to determine whether or not an object in an image field is an offending object. An "offending object" herein is any physical, identifiable structure or shape that is targeted for action. Examples of offending objects may include, but are not limited to, stationary insects, dirt, mold growth, plant features, product imperfections, drones, flying insects, etc. The device is programmed to take an action once an offending object is detected. "Action" can refer to any remedial steps taken by the device to eliminate or otherwise address the offending object. For example, in one embodiment, the action head 18 of device 10 advances to a location of an offending object and it records the spatial coordinates of the same. The coordinates are stored for later treatment and or elimination.

Figure 2:
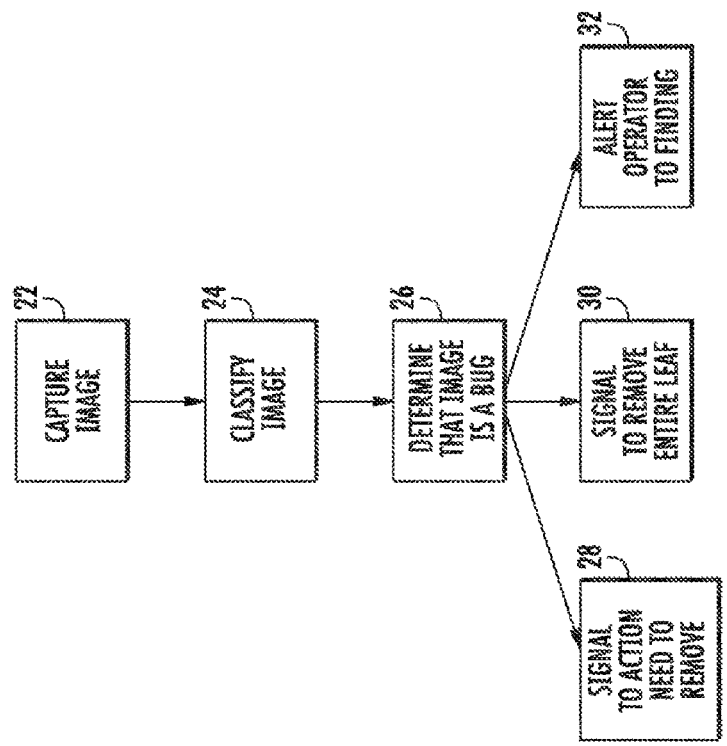
FIG. 2 is a flow chart showing software processing operations according to an illustrative embodiment.

FIG. 2 shows a number of processing steps performed by the software in accordance with an illustrative embodiment. The device is initiated and begins capturing images 22. The images are sent to an image recognition system which classifies various images 24. The classifier may be an algorithmic classifier or a neural network system. The image recognition system is trained to recognize morphological/physical characteristics of bugs or other objects to be detected. The image recognition may also be trained to detect pixel concentrations which may indicate the presence of bug or other objects of interest.

If an image is determined to be a bug 26, then the software performs further processing operations. In one embodiment, the software sends a signal to the moveable arm 28, which directs the action head to the location of the bug to remove the same according to the teachings described above. In another embodiment, the software sends a signal to the moveable arm to push aside the item 30 upon which the bug was detected. Still in another embodiment, upon detecting a bug, the software sends or sounds an alert to a human operator 32. The human operator may intervene to remove the bug or the item.

In another illustrative embodiment, the device can be specifically designed to deal with only one kind of insect on one kind of food or other material, or one other type of offending object. A single kind of action suitable for the situation can be built into such a device.

Extension to a more sophisticated device can be implemented with software taught to deal with many different kinds of foods and materials, to recognize a range of different insects or objects, and different means of removing the insect, including a vacuum, a glue head, an electrical charge, freezing, heat, or even a drop of powerful insecticide. Powerful pesticides sprayed or deposited over a large area are harmful, but a targeted drop on the insect itself will dispatch the insect and not significantly affect the surrounding atmosphere.

In another embodiment, the system can include an array of lenses and response heads so that a sheet being inspected for bed bugs can be continuously passed under the array.

In another embodiment, the system may be used to remove offending objects, such as bugs, from a fluid. In one embodiment, an image capturing device is fixed above a channel of flowing liquid. The device may include an array of image capturing devices or lenses suspended above a channel or similar fluid stream. It will be understood that in one embodiment, the action head may be a vacuum head or suction head such that when the image recognition system detects a presence of an offending object, the software sends a command to the action head to vacuum an area of fluid in the vicinity of the offending object. The vacuum head or suction head can then draw in the offending object, and possibly, some of the surrounding fluid and discard the same.

The present system may be used in any of various environments in which subtle changes need to be detected and then acted on. For example, the beginning of a disease affecting trees or other plants and its subsequent spread is often the result of an insect, beetle or bug penetrating the bark or other surface and destroying the structure from within. Detecting a presence of a specific kind of invader is virtually impossible if it requires a human observer's continued close observation. The instant embodiments can be deployed in a manner which detects and acts whenever an invader is detected on the surface. For example, the software may be trained to detect specific bugs or locusts. Once detected, the software sends a command to spray an offending substance or a pesticide.

In another embodiment, the software is programmed to detect swarms of bugs or other flying objects—irrespective of the type of bugs or objects. In one example, the software is trained to detect a plurality of distinct moving objects within an area of interest. Once a threshold number of moving objects (e.g. >10) is detected, the software will confirm a presence of a swarm and it will automatically send instructions to the action head to address the swarm. In one embodiment, the action head will spray a mist of water vapor or insecticide, smoke laced with insecticide, repellant or similar offending substances. Alternatively, the device can be configured to sound an alarm to disperse the swarm.

The system described herein can be modified to recognize the sign of incipient disease on the skin of a human being at a size that is invisible or almost invisible to the human eye. It is evident that the principles of the proposed systems can be readily applied to other areas where detection, recognition, and action upon a flaw, intrusion, or incipient flaw at a stage where it is barely visible.

Depending on the specific use, the described systems can be associated with a variety of platforms, both mobile and stationary. For example, the image capturing lens and action head may be mounted to a movement mechanism such as a linear guide track, a pulley system, a rack and pinion or any such similar movement mechanisms. Alternatively, the device may be attached to or embedded within a drone, hovercraft, aircraft or similar dirigible. (Mechanical devices/mechanisms for moving the device can be referred to as "movable platforms" herein.) In one in which the device is mounted to a movement mechanism, the software may be programmed to move the device in any of various predetermined or random movements. In such an embodiment, once an offending object is detected, the software sends a command to interrupt movement of the device and deploy the action head to execute one or more remedial actions.

Control of any of the mobile or active platforms envisioned above can be implemented in a variety of ways, including voice recognition. Additionally, the devices and systems described herein, as well as any attendant platform or support, can be supplied with energy in a variety of ways, including batteries, solar, electromagnetic and hard wires, among others.

The proposed systems and devices are not limited to any specific materials of construction or size, and are readily modified by change in programmed recognition patterns to react to different insects, insect parts, plants, plant parts, flying objects, and in some embodiments, to detect extremely small predictable defects or imperfections, among others, in the manufacturing process or in manufactured products. In this latter use, more than one device can be connected to work in tandem, or in any manner called for by the situation.

In one embodiment, the device is furnished with assisted illumination to extend its use at night, through the use of light and infrared, among others. To extend its use further, x-ray and other surface penetrating radiation can be attached to the platform or to the device itself. The image recognition and instant response features of the system can also be incorporated into or provided on the platform.

In one embodiment, a robot platform or movable platform may be provided with an image magnification device to magnify an image of an area, segment and/or substrate to detect objects it is trained to detect.

It is to be understood that in addition to observing and capturing images, the robot or movable platform may be programmed to provide an active response to remove, mitigate and/or react to various conditions. Any of a variety of actions may be deployed by the robot such as, but not limited to, sending an alert or an update, and/or expelling a spray or substance such as pesticide, vapor or smoke. For example, in some embodiments a movable platform such as a robot, vehicle, or drone is utilized to travel about a field, orchard or forest and obtain images of plants and/or trees growing therein. The software detects any of various conditions associated with plants and/or trees and is trained to react accordingly. In one embodiment, the device is trained to detect boring insects (e.g. Emerald Ash Borers) by recognizing physical features such as appearance, color, size, shape etc. Additionally or alternatively, the device detects holes in plants or trees created by such insects. The device then automatically responds by directing the action arm to the detected insect or its entry hole. For example, in one embodiment, the device directs the action arm to an entry hole formed by boring insects and releases a blast of white paint or similar marking material to mark the tree for removal or for remedial treatment.

In a further implementation, the device is programmed to provide an instant response which results in recognition and capture instead of recognition and reject. That is, objects, such as insects, which are of interest instead of being offending, can be trapped and captured with the same device, using only a modification. That is, rather than dispersing or deflecting an object of interest, the software sends a signal to the mechanical arm to capture and maintain the object of interest.

The device may also be deployed for use in quality control activities. In this embodiment, the device may be trained to recognize qualitatively acceptable objects and those that do not meet acceptable criteria (or "defective objects"). The software is programmed to employ an action head to capture defective objects. Acceptable criteria may be any of size criteria, shape criteria or such similar metrics calculated by the software or algorithmic classifier. In other embodiments, acceptable criteria may be based on color criteria, pixel counts, pixel saturation or any such similar image criteria the software and image recognition/analysis software is programmed to analyze.

The devices and systems described herein can also be used as a stand-alone, hand held devices, or devices that are fixed in place with items to be inspected passing through. In one embodiment, the lens/image capture device and action heads can be in a circular or other convenient pattern, and on both sides of the material, as on both sides of a sheet.

In one embodiment, the proposed device is attached to a drone which is programmed to move up and down, and all around a tree periodically, and subsequently to move on to other trees. This will enable the device to protect forests, orchards, and plantations against invasive species. Drones can be programmed to travel in certain sectors of a forest or orchard, around a periphery or in any pattern as designated by an operator to capture images in the area below it and instantly react.

A drone can also be programmed to remain stationary, detecting and protecting against the arrival of an expected invasive species for which it has been trained. Similarly, attaching the device to a robot enables the protection against land based invasive species in addition to airborne species.

In each case, the proliferation of robots and drones, as well as other platforms, extends the use and effectiveness of the device. Included in such other platforms are hovercrafts, extendable legs and floatable devices among others known to those skilled in the art.

Figure 3:
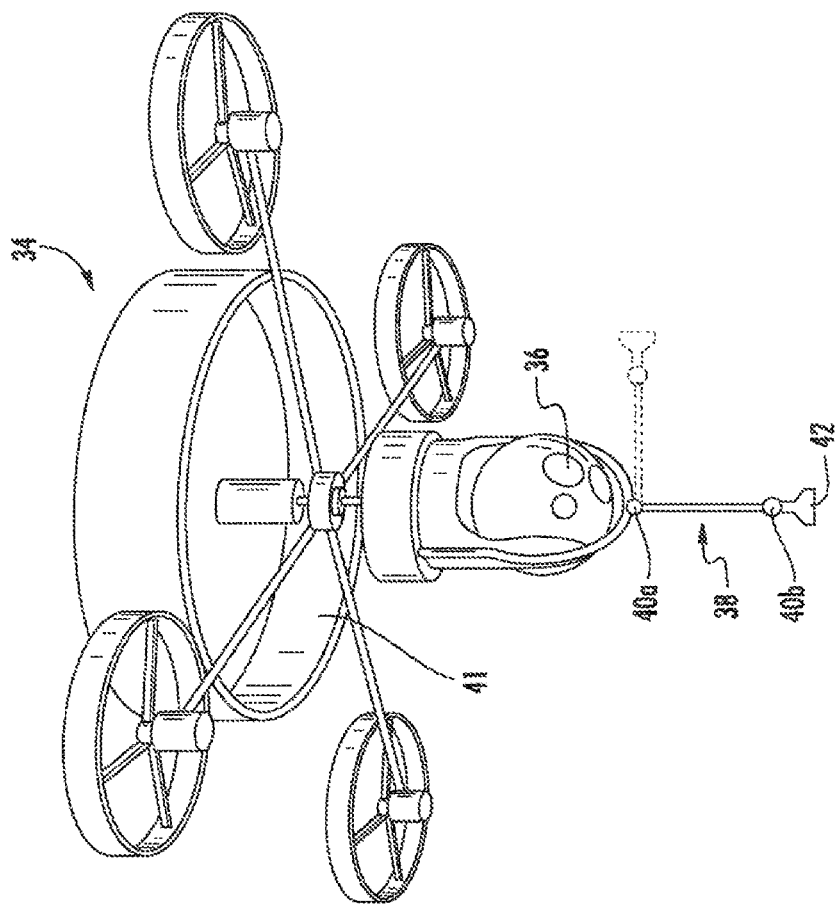
FIG. 3 shows a side perspective view of a scanning device incorporated with a drone according to an illustrative embodiment.

FIG. 3 shows a drone 34 used to capture images and provide an active response according to an illustrative embodiment. Drone 34 has an image capturing device for capturing images of areas to be analyzed. For example, as shown, drone 34 has a lens 36 which is part of a camera or video camera. In one embodiment, the image capturing device is housed in a movable and/or rotatable housing. The lens 36 captures images, which are then analyzed by the image analysis software. The image analysis software may be located in a computer residing in the drone 34 or images may be sent via wire or wireless communication to a computer at another location.

An action arm 38 is shown extending from the body of the drone 34. Action arm 38 has one or more rotatable joints 40a, 40b, ball joints or similar pivoting members allowing for various movement of the action arm 38. For example, in the embodiment shown, action arm 38 is shown pointing downward in an orientation substantially orthogonal to the body 41 of the drone, but it could be rotated around joint 40a to a 90.degree. angle.

An action head 42 is shown positioned at the terminal end of action arm 38. The software is configured to direct action head 42 in the direction of a detected offending object and to automatically initiate remedial actions. For example, action head 42 is activated to expel any of various substances described above in response to a command from the software. A tank or similar storage reservoir within the drone stores substances to be dispersed or dispensed from the drone.

In another embodiment, drone 34 is used to capture images of plants or features of plants and to disperse pollen in response to such detection. In some embodiments, the system detects images of plants such as flowers and trees to determine whether or not the plant is a flowering plant adapted for receiving pollen. Additionally or alternatively, the system detects plant objects or features that are adapted to receiving pollen. Upon detection of such plants and/or upon the detection of reproductive features of flowering plants—the drone automatically dispenses pollen. In one embodiment, the pollen is directed to the approximate location of detected flowering plants, but in other embodiments, the pollen is directed to an area proximate to a detected flower or reproductive feature.

In an illustrative embodiment, an image capturing mechanism is used to capture images of plants, trees or other vegetation and image analysis software is utilized to detect objects consistent with flowering plants. As will be understood by those of ordinary skill in the art, the image analysis software may be located in a computer residing in the drone 34 or images may be sent via wire or wireless communication to a computer at a remote location. The image analysis software determines whether or not a plant is one that is adapted to receive pollen and/or whether or not a plant feature is an organ that is adapted to receive pollen (such as a pistil).

In some embodiments, the drone 34 may be directly controlled by a human operator, whereas, in other embodiments the drone is controlled by one or more computers. The drone 34 flies over areas of vegetation and its image capturing system scans the terrain below. In some embodiments, as described above, the image analysis system is trained to detect specific plants for purposes of pollination. In other embodiments, the image analysis system is additionally or alternatively trained to detect specific plant features that are adapted for receiving pollen.

In another illustrative embodiment, once a particular plant-type is detected, the system is programmed to release pollen in the vicinity of such detected plants. That is, once a plant of interest is detected, the software sends a command to the drone to navigate toward such plants and to release pollen.

In other embodiments, the system is programmed to detect specific plant features, like pistils. Once a pistil is detected, the program sends a command to an action arm to release pollen in the direction of the detected pistil. Action arm 38 is shown extending from the body of the drone 34. Action arm 38 has one or more rotatable joints 40*a*, 40*b*, ball joints or similar pivoting members allowing for various movement of the action arm 38. For example, in the embodiment shown, action arm 38 is shown pointing downward in an orientation substantially orthogonal to the body of the drone, but it could be incrementally rotated around joint 40*a* to a 90 degree angle in order to more accurately point the action head 42 in the direction of a pistil.

Action head 42, shown positioned at the terminal end of action arm 38, is provided with a nozzle or such similar spout for releasing a cloud, mist or similar stream of pollen. The software is configured to direct action head 42 in the direction of a flower to be pollinated and automatically expel pollen in the direction of the plant of interest, flower of interest, or plant feature of interest. A tank or similar reservoir within the drone stores substances to be dispersed or dispensed from the drone.

In one illustrative implementation, the system is programmed to detect features associated with almond trees. In this embodiment, once the software confirms a presence of an almond tree, it will automatically send instructions to navigate the drone 34 to an area proximate to the almond tree and subsequently send instructions to the action head 42 to release pollen. In one embodiment, the software is trained to identify flowers on almond trees and to disperse pollen on or near respective flowers. In other embodiments, the system is trained to detect respective reproductive features on flowers of the almond tree (such as pistils) and the action arm is instructed to direct the action head 42 toward the reproductive features. Once the action head is properly oriented, a command is sent to expel a spray or mist of pollen.

In another illustrative embodiment, the software is trained to recognize a specific pistil and initiate a dispersal of pollen that is specific to the pistil of interest. In another embodiment, reservoirs of different pollen types are provided on the drone or similar movable device. The software is trained to recognize and detect a variety of different flowers/pistils (associated with different flowers or flower types) and disperse a pollen type that corresponds to the detected pistil.

It will be understood by those of ordinary skill in the art that drone 34 or a similar aircraft, hovercraft or dirigible having an image capturing device in communication with an image recognition system may be used to detect and monitor any of various conditions and instantly react by dispersing any of various substances or performing other actions via an associated action head. For example, a device may be programmed to detect plant conditions or soil conditions (e.g. using color properties thereof) and to automatically disperse water or nutrients to the detected areas when a dry soil condition or an unhealthy plant condition is detected. In other embodiments, a device may be programmed to detect fires. For example, a drone may be programmed to fly over a forested area and detect visual indicia of smoke or fire. Additionally or alternatively, the device may have a heat sensor to detect fires. Once a fire is detected, the device is programmed to navigate into proximity of the fire and automatically disperse fire retardants such as chemicals or water.

In an illustrative embodiment, the computer which operates the device may operate under the control of an operating system and software applications, components, and programs that execute the routines and systems described herein. In general, the routines executed to implement the embodiments, whether implemented as part of an operating system or a specific application, component, program, object, module or sequence of instructions will be referred to herein as "the system", or "software". The software can control the image acquisition, image storage, image analysis and movements of the arm, action head and/or the movement of the device along a track or other movement mechanism.

Figure 4:
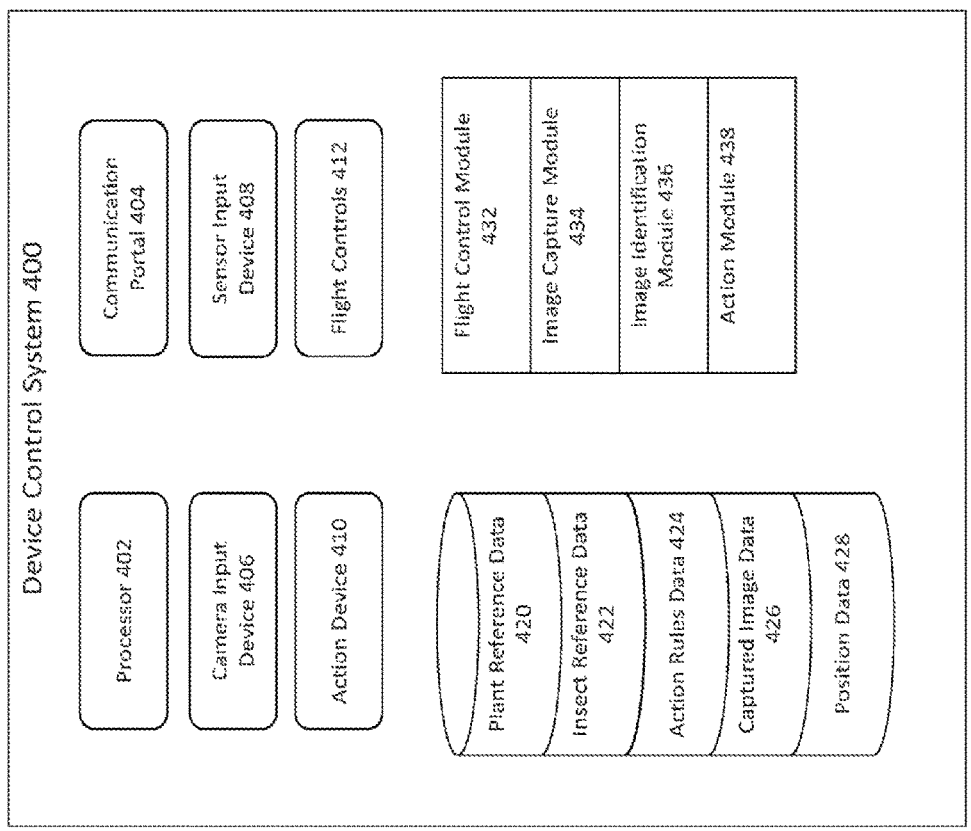
FIG. 4 is a schematic diagram of a device control system according to an illustrative embodiment.

FIG. 4 is a schematic diagram of a device control system 400 in accordance with an illustrative embodiment. The device control system may include a computer system having one or more computers. The device control system may govern operation of an imaging and/or image evaluation device, as may be employed by an imaging drone as described herein. In some embodiments, certain components of the device control system 400 may be located on-board the device, such as on or within a drone, or remotely, such as at a remote computer system, which may be accessible via a data network. For example, the image identification module 436 and/or action module 438 may be located remotely, e.g., on one or more servers. Image data may be uploaded (via physical connection of memory storage devices and/or wirelessly) to the image identification module 436 for evaluation. In some embodiments, action instructions may be transmitted by an action module 438 to one or more drones for execution.

The device control system 400 may include hardware, such as one or more processors 402, a communication portal 404, one or more camera input devices 406, one or more sensor input devices 408 (e.g., scanners, range finders, position sensors (e.g., GPS receivers, altitude sensors, to name a few)), action device 410 (e.g., action head and/or movable arm, as described herein), and/or flight controls 412. Flight controls 412 can include thrusters, engines, motors, turbines, fans, rotors, propellers, thrust vectoring control surfaces, aerodynamic control surfaces, and/or actuators and/or servo motors to move such hardware components. In some embodiments, a drone can include wheels, treads and tracks, or other ground propulsion systems, including motors. In other embodiments, the drone can be designed to float and thus may include floatation devices (e.g., pontoons) or buoyant exterior components of the drone, as well as a water propulsion system.

The device control system 400 may further include non-transitory computer-readable memory (e.g., local and/or remote), which may store and/or access data, e.g., in one or more databases. Such data can include plant reference data 420, insect reference data 422, action rules data 424, captured image data 426 or other sensor data, and/or position data 428, as described herein. The device control system 400 may also include one or more software modules stored in the memory and configured to execute machine-readable instructions to perform one or more processes. Such modules can include a flight control module 432, image capture module 434, image identification module 436, and/or action module 438. The processes and functions described with respect to each module may be performed by one or more other modules, such as other modules described herein or additional modules.

The communications portal 404 may handle, process, support, and/or perform wired and/or wireless communications, such as transmitting and/or receiving data (e.g., data packets). In embodiments, transmission described with respect to a single data packet may comprise a plurality of data packets. Data packets may be discrete electronic units of data. In other embodiments, transmissions may comprise non-discrete signals, such as data streams. Transmissions described with respect to data packets may also comprise data transmissions via other communications mechanisms known in the art, such as data streams. Communications portal 404 can comprise hardware (e.g., hardware for wired and/or wireless connections, such as communications chipsets, communications interfaces, and/or communications antennas, to name a few) and/or software.

Wired connections may be adapted for use with cable, plain old telephone service (POTS) (telephone), fiber (such as Hybrid Fiber Coaxial), xDSL, to name a few, and wired connections may use coaxial cable, fiber, copper wire (such as twisted pair copper wire), and/or combinations thereof, to name a few. Wired connections may be provided through telephone ports, Ethernet ports, USB ports, and/or other data ports, such as Apple 30-pin connector ports or Apple Lightning connector ports, to name a few.

Wireless connections may include cellular or cellular data connections and protocols (e.g., digital cellular, PCS, CDPD, GPRS, EDGE, CDMA2000, 1.times.RTT, Ev-DO, HSPA, UMTS, 3G, 4G, 5G, and/or LTE, to name a few), Bluetooth, Bluetooth Low Energy, Wi-Fi, radio, satellite, infrared connections, ZigBee communication protocols, to name a few. Communications interface hardware and/or software, which may be used to communicate over wired and/or wireless connections, may comprise Ethernet interfaces (e.g., supporting a TCP/IP stack), X.25 interfaces, T1 interfaces, and/or antennas, to name a few.

Turning to the data that the device control system 400 may store and/or access, plant reference data 420 can include one or more images of each of a plurality of species for image comparison purposes and/or an identifier or database association to indicate the respective species associated with each image. In embodiments, the plant reference data can include images of plant parts, such as a pistil, petal, or leaf, to name a few. Plant reference data can also include growing condition data, which may be coupled with GPS data of captured images to narrow the number of reference images that are likely to produce a match. Growing condition data can include any of water availability, soil type, temperature information (e.g., temperature ranges), climate, geographic location information, etc.

Insect reference data 422 can include one or more images of insects of various species or insect components (e.g., wings) and an indicator or reference to associate each image with its respective species. Insect reference data may include size information (e.g., cross-sectional measurements, measurements of body components, such as body segments, antennas, legs), body information (e.g., number of body segments, number of antenna), color information, geographic information (e.g., indicating where the insect is likely to be found), habitat information (e.g., indicating habitats in which the insect is likely to be found, such as they type of crops, type of terrain, temperatures), and/or food source information.

Action rules data 424 can comprise rules to control an action device 410 (e.g., to control movement and/or usage of the action device 410) and/or logical rules to govern when to use the action device 410.

Captured image data 426 can comprise one or more images (e.g., image files), sequences of images, and/or videos (e.g., video files). Captured image data 426 may be associated with position data indicating a position of the subject of the image and/or a position of the drone or camera. The device control system 400 may further store and/or access additional sensor data from other sensor input devices 408, such as range information (e.g., from the drone or camera to an image subject), infrared imaging data, heat imaging data, temperature information, and/or ambient light intensity information, to name a few.

Position data 428 can include global positioning coordinates (e.g., indicating latitude, longitude, and/or altitude or elevation), street address information, and/or local coordinate information (e.g., one, two or three-dimensional locations in relation to the drone or camera).

A flight control module 432 may control movement of a drone, such as by controlling thrust, control surfaces or other flight control hardware 412.

An image capture module 434 may govern when and how to capture images (e.g., which subject to focus on, zoom level, type of imagery to capture (still versus video), and/or number of images to capture, etc.).

An image identification module 436 or image classifier may perform image analysis, such as comparisons to reference images and/or reference data as described herein, to detect one or more subjects in a captured image, such as plant species, insect species, insect quantities, and/or other foreign objects.

An action module 438 may evaluate action logical rules with respect to captured and processed image data to determine one or more actions to take. The action module may also control one or more action devices (e.g., such as an action head and/or movable arm attached thereto) to cause them to carry out the determined actions.

Figure 5:
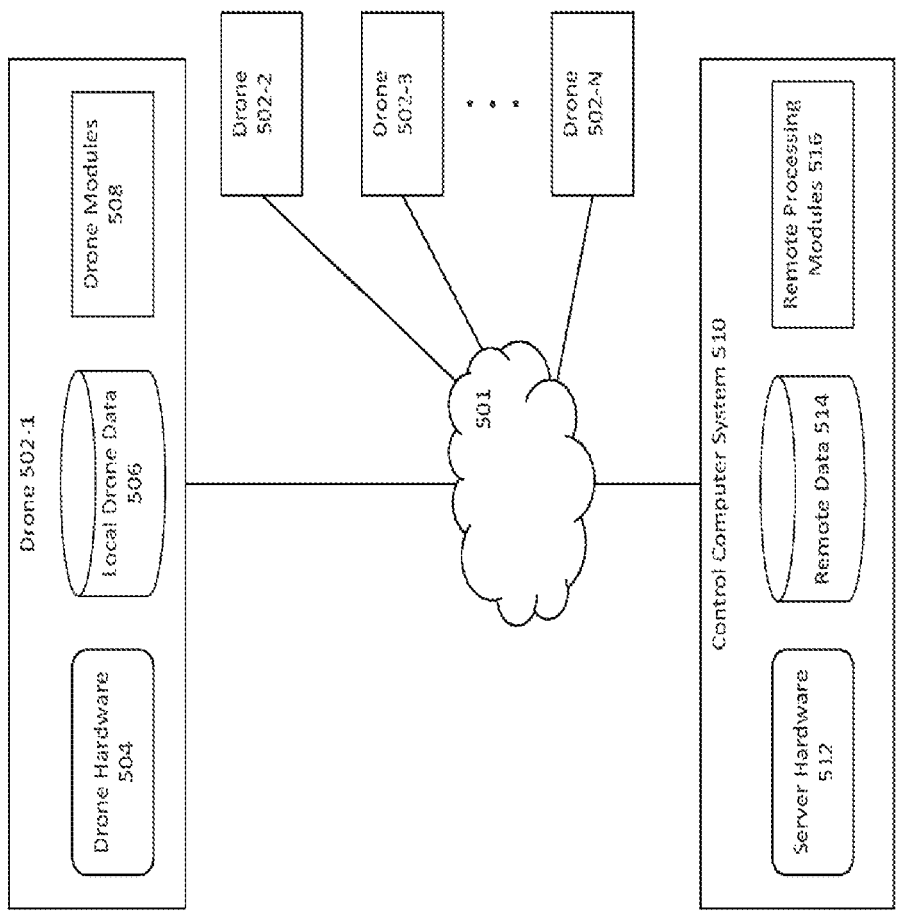
FIG. 5 is a schematic diagram of a drone scanning system according to an illustrative embodiment.

FIG. 5 shows a schematic diagram of a drone scanning system in accordance with an illustrative embodiment. The system can comprise one or more drones 502 (e.g., drones 502-1, 502-2, . . . 502-N) and/or a control computer system 510, which may be remotely located, such as on one or more servers. The devices (e.g., drones) and/or computer systems may be operatively connected directly, e.g., via wired or wireless communications, and/or indirectly, e.g., via a data network 501, such as the Internet, a telephone network, a mobile broadband network (e.g., a cellular data network), a mesh network, a local area network (LAN) (including a wireless local area network, e.g., a Wi-Fi network), a wide area network (WAN), a metropolitan area network (MAN), and/or a global area network (GAN), to name a few. Data networks may be provided via wired and/or wireless connections. Data networks may be public or private. Accordingly, data networks may be open or closed, such as requiring authorized access, specific communication connections, or specialized hardware and/or software. In some embodiments, any combination of communications channels may be utilized.

Processing of data from one or more drones 502 and/or control of each drone may be performed by one or more respective processors contained within or on each drone, one or more processors contained within or on one or more master drones that transmit commands to subordinate drones, and/or performed remotely such as at a remotely located control computer system, which may be one or more servers comprising one or more computers that receive data from and/or transmit instructions to the drones. In embodiments, any of the data processing and/or device control functions may be divided among entities, such as the drones 502 and remote control computer system 510. For example, flight controls or vehicle movement may be handled at each device, while image processing may be performed remotely. In embodiments, data acquisition may be handled at the device (e.g., capture of images and/or sensor data) and transmitted to the remotely located control computer system 510. The computer system 510 may process such data as described herein (e.g., perform image recognition and/or determine actions), and/or transmit instructions (e.g., action instructions, which may be machine-readable instructions to execute one or more determined actions) to the device 502 or to one or more other devices. Accordingly, one or more first drones 502 may acquire data while one or more second drones 502 may execute actions based upon determinations from the acquired data.

Both drones 502 and the control computer system 510 may include one or more processors, memory devices storing data in non-transitory computer-readable memory, which data may be organized in one or more databases, and communication portals (e.g., communications antennas and/or chipsets, as described herein). Drones and the control computer system may further comprise one or more input devices, e.g., to receive direct user input. Accordingly, drones may have keypads, touch screens, buttons with hardwired or programmed functionality, microphones, cameras (e.g., with gesture processing software), or other input devices. The control computer system 510 may include one or more input devices such as keyboards, mice, touchpads, touchscreens, microphones, cameras, etc., and/or output devices (e.g., display screens or speakers, etc.).

Each drone 502 may also include the respective hardware 504 (e.g., cameras, sensors, vehicle propulsion and control hardware), data 506 (e.g., rules for autonomous movement or control, flight path data, reference imagery and/or data, and/or captured data), and software modules 508 (e.g., any of the software modules described with respect to FIG. 4) to operate in such a divided control system.

Similarly, the control computer system 510 can include the hardware 512 (e.g., processors, memory devices, and/or communication portals), data 514, and/or software modules 516 running on one or more processors to perform its assigned functions. Accordingly, remote data 514 can include databases of reference imagery and/or other reference data, which may be used in image analysis. Remote data 514 can also include a repository of captured images and/or other sensor data, such as from across time periods and/or from a plurality of drones.

Remote processing modules 516 may include flight control modules, e.g., for controlling navigation routes or destinations, image analysis modules, and/or action modules to determine actions to take. The remote control computer system 510 may receive data from one or more drones, store such data, process such data, and/or generate and transmit machine-readable instructions to the drones.

As discussed above, in one embodiment, the device is an apparatus having image capturing capabilities and image recognition capabilities coupled with software that is programmed to determine whether or not an object in an image field is a pistil. A "pistil" herein is any physical, identifiable structure or shape of a plant part that is adapted to receive pollen. Once a pistil is detected, an automatic response in an action arm directs pollen to the identified pistil.

As also discussed above, the device set forth herein may be programmed to provide an active response to remove, mitigate and/or react to various biological conditions. For example, in some embodiments, the device may be programmed to detect a presence of skin conditions and send an alert or expel a marking material to a body site where a condition is identified. In an illustrative embodiment, the device is programmed to detect ticks embedded on user's skin by recognizing physical features consistent with ticks, such as appearance, color, size, shape etc.

The tick-detecting device may be disposed on a movable platform, for example, as set forth herein, and programmed to move across an external aspect of a person or of a limb. In other embodiments, the device is a handheld unit that is grasped and manipulated by a user.

When a tick, bite, or mark is identified, the device automatically responds by directing the action head to the location of the detected tick and releases a blast of degradable ink, paint or similar marking material to designate a need for careful inspection or removal as the case may be.

In some embodiments of the invention, the device is programmable to be tailored to identified users for more specific tick detection. In such embodiments, the device is initially deployed to image the entire skin surface of a given user. The device detects all images that contrast with normal skin tone, and stores each of the images in a database (e.g. on a digital storage medium). Thus, after initial deployment, the system's database will have images of each mole, scar, or other dark marks on the user's skin. Upon subsequent deployment, the system will search for contrasting images and compare each contrasting image detected against the stored database. If a match is found, then the system can determine that the detected image was previously present on the user and no action is necessary. If, however, an image is detected for which there is no match—the system will then direct the action head to mark the newly found image. In this embodiment, a tick will present as an image for which there is no corresponding match, and it will trigger a response of the action head as set forth above.

Still in other embodiments, the device set forth herein may be programmed to provide an active response to remove, mitigate and/or react to various agricultural conditions.

For example, the device may be deployed in a field, garden, or orchard to detect early indications of weeds or similar harmful plants. The device may be provided on a stationary structure to scan an area of a field. Alternatively, the device may be mounted on a movable platform such as a robot, vehicle, or drone that is utilized to travel about a field and obtain images of plants growing therein. The software is programmed to distinguish between a weed and a desired crop or plant. When it detects any of various features associated with weeds or other undesired vegetation it will automatically react. In one embodiment, the device is trained to detect weeds by recognizing physical features such as appearance, color, size, shape etc. In the event that weeds are detected, the device automatically responds by directing the action arm to the detected weed or plant and releasing herbicide to the vicinity of the detected weeds.

In another illustrative embodiment, the devices and systems described herein can be in the form of a security system used to identify and/or target other offending objects, such as drones and other mechanical devices which can move in the air, on the ground, or through the water. Such security systems can be used to keep an area secure and/or free from threats. For example, such a security system can be used by a prison to prevent drones from flying over prison grounds and delivering contraband to prisoners. Such a security system can also be used to help protect military bases, bunkers, supply caches, communication towers, homes, etc. from spying and/or attacks implemented using mechanical devices.

In one embodiment, a security system can include a mobile platform that allows the system to traverse land, air, and/or water. For example, the system can include tracks that allow the mobile platform to move along the ground, propellers or other thrust component to allow the mobile platform to move through the air, and/or lightweight inflatable pontoons using in conjunction with a thrust component that allows the mobile platform to float and move through the water. The system can also include one or more image capture devices, one or more processors, one or more computer memories, one or more communication components for communicating with remote systems, control and logic software, and/or one or more detectors such as motion detectors, sound detectors, wireless signal detectors, one or more action arms, etc. mounted to the mobile platform.

The one or more image capture devices for the security system can include still cameras, video cameras, infrared imaging devices, x-ray imaging devices, magnification lenses, etc. that are configured to capture images of a given area. Captured images/data can be stored in a computer memory of the security system and/or transmitted to a remote storage/processing system using the communication components. The computer memory of the security system can also be used to store the control and logic software, which can be used to identify objects and make determinations regarding what, if any, action is to be taken upon identification of an object. The logic can include image recognition software that can be used to analyze images/video captured by the system to determine if any offending objects are present. The control and logic software can be executed by the one or more processors of the system. In an illustrative embodiment, the security system can be configured to determine whether an identified object is a living object (i.e., person, bird, animal, etc.) or an inanimate object (drone, robot, etc.). The action taken by the system can be based in part on whether the object is living or inanimate.

The one or more sensors of the security system are used to detect the presence of objects and to help determine whether detected objects are considered offending objects. A motion detector sensor can be used to identify motion, which can be indicative of an approaching object. A microphone or other noise detector can be used to detect sounds which can be indicative of an approaching object, such as motor noise, propeller noise, electronics noise, voices, etc. A wireless signal detector can be used to detect approaching objects based on wireless signal transmissions made by the approaching object. The security system can also include a temperature probe detector for determining the temperature at or near an approaching object. The security system can also include an infrared detector to detect whether an approaching object is releasing any heat.

Figure 6:
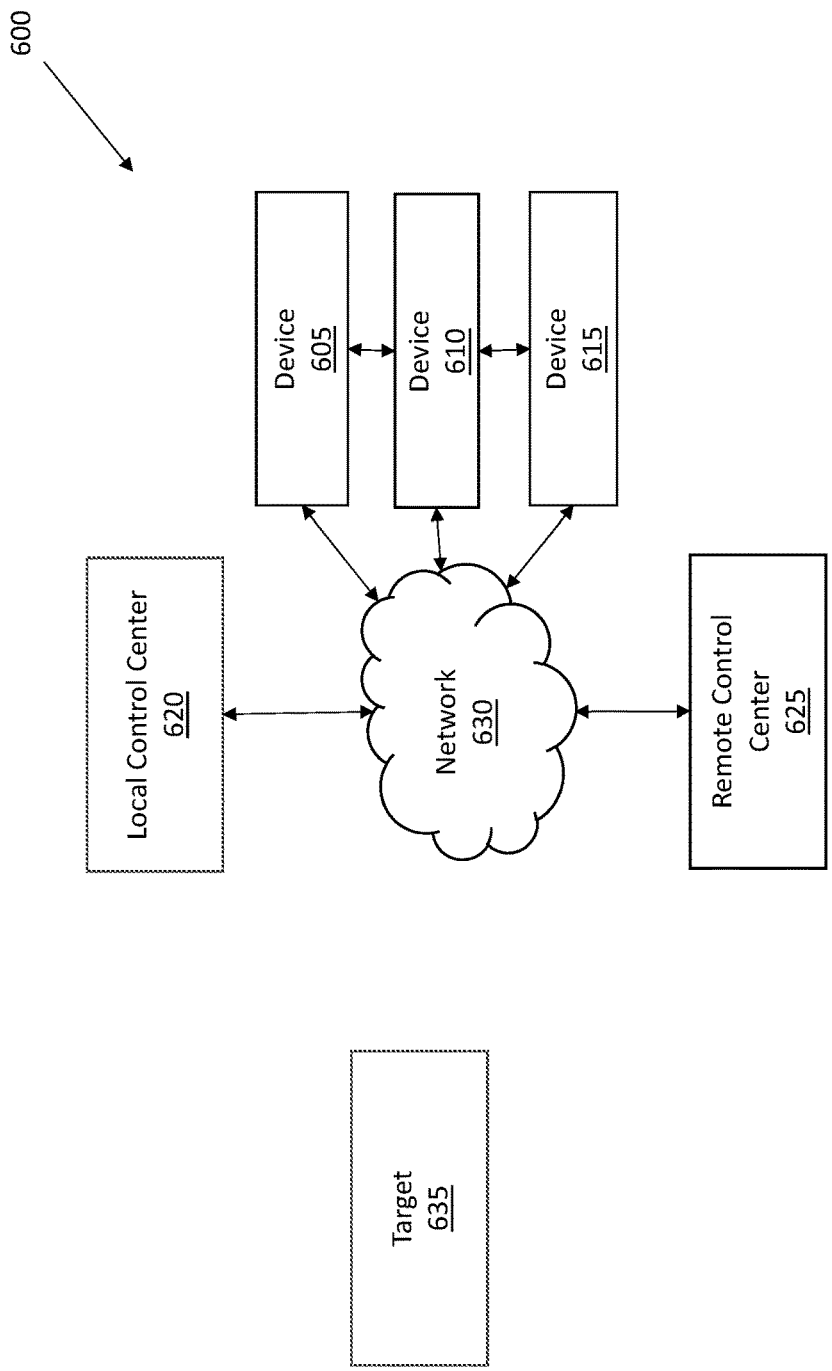
FIG. 6 is a block diagram depicting a system to target mechanical offending objects in accordance with an illustrative embodiment.

FIG. 6 is a block diagram depicting a system 600 to target mechanical offending objects in accordance with an illustrative embodiment. As depicted, the system 600 includes a device 605, a device 610, a device 615, a local control center 620, a remote control center 625, and a network 630. In alternative embodiments, the system 600 can include fewer, additional, and/or different components. In an illustrative embodiment, each of the devices 605, 610, and 615 can be mechanical devices which are configured to monitor an area and take action based on the monitoring. The area being monitored can be a school, a prison, a government building, a home, a business, a warehouse, a military base, etc.

In an illustrative embodiment, each of the devices 605, 610, and 615 can include a mobile platform, an image capture device, one or more sensors, a processor, a memory, a transceiver, a power source, and an action arm. The mobile platform can allow the devices 605, 610, and 615 to fly through the air, to move along the ground, and/or to float and move on water. As such, each of the devices 605, 610, and 615 can be in the form of a drone, watercraft, wheeled vehicle, robot, etc. The one or more sensors on the devices can include motion detector sensors, microphones, temperature sensors, wireless signal sensors, infrared sensors, etc. As discussed above, these sensors can be used to detect the presence of an object and/or to determine whether a detected object is living or inanimate.

The memory of the devices 605, 610, and 615 can be used to store algorithms and operating logic, and the processor can execute the algorithms and logic. The transceiver, which can be controlled by the processor, allows the devices 605, 610, and 615 to communicate with one another, either directly or through a network 630. The transceiver also allows the devices 605, 610, and 615 to communication with the local control center 620 and the remote control center 625. The network 630 can be any type of network known in the art, such as a cellular network, a short-range communication network, a radio frequency network, the Internet, etc.

The local control center 620 can be proximate to the area being monitored, and can include docking stations or other components to periodically charge the power sources of the devices 605, 610, and 615. The power sources can be in the form of batteries or any other charge generating/storing devices. The local control center 620 can also include at least a processor, memory, and transceiver. The local control center 620 can be configured to receive images/video captured by the image capture device and data detected by the sensors, and can process that received data to determine whether a possible target, such as a target 635, is present. In the event of a possible target, the local control center 620 can generate instructions for one or more of the devices 605, 610, and 615 to take action. In an alternative embodiment, each of the devices 605 may perform data processing on-board and may make independent decisions regarding any action to be taken.

In another embodiment, any of the processing and/or decision-making can be performed by the remote control center 625. The remote control center 625 can be located in a remote position relative to the area being monitored by the system. As one example, the remote control center 625 can be a hub/facility which is tasked with the monitoring of a plurality of different locations. In one embodiment, data processing and instruction generation can normally be performed at the local control center 620 or on-board the devices 605, 610, and 615, but can be overridden by the remote control center 625 for sensitive or particularly important scenarios. In an alternative embodiment, the remote control center 625 may not be included.

In an illustrative embodiment, one or more of the devices 605, 610, and 615 can identify the target 635 using its image capture device and/or other sensors. The target 635 can be a drone or other mechanical device, a person, or an animal. Upon detection of an object, the system determines what, if any, action is to be performed by the devices 605, 610, and 610. In one embodiment, the system 600 determines whether the target 635 is living or inanimate and bases the action determination on the result. For example, if the target 635 is determined to be living, the system 600 may perform one or more notification operations to alert appropriate individuals of a person or other living thing the area that is being monitored. If the target 635 is determined to be inanimate, the system 600 can instruct one or more of the devices 605, 610, and 615 to take action using their action arms.

In one embodiment, if a determination is made by the system 600 to take action, one or more of the devices 605, 610, and 615 is instructed to use their action arms to capture or disable the target 635. The target 635 can be captured by a net that is launched from an action arm of one of the devices, and that is configured to inhibit further movement of the target 635. The action arm can also be used to fire a projectile at the target 635 to disable it. The projectile can be a bullet, a rubber bullet, a bean bag, a paint ball, an arrow, or any other type of projectile. In one embodiment, the action arm can include a flame thrower that is configured to direct fire toward the target 635. The action arm can also include a laser that is configured to direct a laser beam at the target 635 to disable or destroy it. The action arm can further include a signal jammer or interference unit that is designed to disable wireless communications from being transmitted or received by the target 635.

It should be understood that the disclosed embodiments have been described to provide the best illustration of the principles of the subject matter and its practical application to thereby enable one of ordinary skill in the art to utilize the system in various embodiments and with various modifications as are suited to the particular use contemplated.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A device for use in a security system, the device comprising:
   a sensor;
   an image capture device;
   an action arm; and
   a processor in communication with the sensor, the image capture device, and the action arm, wherein the processor is configured to:
      receive data from the sensor and the image capture device;
      identify a target based on an analysis of the received data;
      determine, based on the analysis of the received data, that the target is a drone or other mechanical device;
      determine an action to take on the identified target; and
      cause the action arm to perform the determined action on the target.

2. The device of claim 1, wherein the processor is located remote from the device at a control center.

3. The device of claim 1, wherein the processor is positioned at a local control center for the device, wherein the local control center includes a docking station for the device.

4. The device of claim 1, wherein the sensor comprises one or more of a motion detection sensor, a microphone, an infrared detector, and a wireless signal detector.

5. The device of claim 1, wherein the processor is further configured to determine, based upon the received data, whether the target is alive or inanimate.

6. The device of claim 5, wherein the determined action is based at least in part on whether the target is alive or inanimate.

7. The device of claim 1, wherein the action arm comprises a laser, and wherein the determined action comprises directing a laser beam at the target by the laser.

8. The device of claim 1, wherein the action arm includes a net, and wherein the determined action comprises launching the net at the target.

9. The device of claim 1, wherein the action arm is configured to launch a projectile, and wherein the determined action is to launch the projectile at the target.

10. The device of claim 1, wherein the action arm includes a signal jammer, and wherein the determined action is to jam wireless signals such that the target is unable to receive or transmit.

11. The device of claim 1, wherein the action arm includes a flamethrower, and wherein the determined action is to burn the target using the flamethrower.

12. The device of claim 1, further comprising a mobile platform that allows the device to move, wherein the mobile platform is in communication with the processor.

13. The device of claim 12, wherein the mobile platform includes at least one of one or more thrust systems that allows the device to fly through air, one or more tracks or wheels that allows the device to move on ground, and one or more floatation units that allows the device to float.

14. The device of claim 12, wherein the mobile platform allows the device to monitor an area, wherein the area is associated with a school, a prison, or a military facility.

15. The device of claim 1, wherein the processor is further configured to perform the analysis of the received data, wherein the analysis includes image recognition processing.

16. A method for implementing a security system, the method comprising:
   receiving, by a sensor on a device, first data indicative of a target;
   receiving, by an image capture device of the device, second data indicative of the target, wherein the second data comprises image data;

identifying, by a processor in communication with the sensor and the image capture device, a presence of the target based on an analysis of the received data first data and second data;

determining, by the processor and based on the analysis of the received data, that the target is a drone or other mechanical device;

determining, by the processor, an action to take on the identified target; and performing, by an action arm of the device that is in communication with the processor, the determined action on the target.

17. The method of claim 16, further comprising positioning the action arm of the device proximate to the target using a mobile platform of the device.

18. The method of claim 17, wherein the mobile platform includes at least one of one or more thrust systems that allows the device to fly through air, one or more tracks or wheels that allows the device to move on ground, and one or more floatation units that allows the device to float.

19. The method of claim 16, further comprising determining, by the processor and based upon the received first data and second data, whether the target is alive or inanimate.

20. The method of claim 16, wherein the action arm includes a net, and wherein the performing the determined action comprises launching the net at the target.

* * * * *